United States Patent [19]

Patel et al.

[11] 4,264,502
[45] Apr. 28, 1981

[54] N-(ARYLTHIOCARBAMOYL)-2-AMINO-1H-ISOINDOLE-1,3-(2H)DIONES AND USE AS PLANT GROWTH REGULATORS

[75] Inventors: Natu R. Patel; Jerry L. Rutter, both of Overland Park, Kans.

[73] Assignee: Gulf Oil Corporation, Pittsburgh, Pa.

[21] Appl. No.: 113,861

[22] Filed: Feb. 5, 1980

Related U.S. Application Data

[63] Continuation-in-part of Ser. No. 19,065, Mar. 9, 1979, abandoned.

[51] Int. Cl.³ .................... C07D 209/48; A01N 43/38
[52] U.S. Cl. .................... 260/326 S; 71/74; 71/96
[58] Field of Search .................... 71/74, 95, 96; 260/326 N, 326 S

[56] References Cited

U.S. PATENT DOCUMENTS

| | | | |
|---|---|---|---|
| 2,945,047 | 7/1960 | Sherman | 260/347.2 |
| 3,318,680 | 5/1967 | Levitt | 71/99 |
| 3,410,842 | 11/1968 | Allais et al. | 260/239.3 |
| 3,455,984 | 7/1969 | Laliberte et al. | 260/465 D |
| 3,511,875 | 5/1970 | Brantley | 71/106 |
| 3,649,638 | 3/1972 | Asato et al. | 260/243.3 |
| 3,712,914 | 1/1973 | Tilles | 71/99 |
| 3,741,746 | 6/1973 | Marrese et al. | 71/99 |
| 3,836,350 | 9/1974 | Fawzi et al. | 71/92 |
| 3,912,496 | 10/1975 | Fawzi et al. | 71/92 |
| 3,940,411 | 2/1976 | Asato et al. | 548/143 |

FOREIGN PATENT DOCUMENTS

| | | |
|---|---|---|
| 1174103 | 9/1962 | Fed. Rep. of Germany . |
| 53-74549 | 7/1978 | Japan . |
| 1272920 | 5/1972 | United Kingdom . |

OTHER PUBLICATIONS

Derwent Abstract of German Patent DT 2163619, Jun. 22, 1972.
G. Meran, Rev. Stiintifica "V. Adamachi", 32, 136–138, (1946).
E. Hoggarth, J. Chem. Soc., pp. 1163–1167, (1949).
P. Pel'kis et al., Zh. Obsch. Khim., 31, 3726–3728, (1961).
S. Amer. Nucleus (Calcutta), (1973), 16(1), 26–28.
N. Buu-Hoi et al., Bull. Soc. Chim. France, (1956), 363–369.
Derwent Abstract of W. German Patent 2,163,619.

*Primary Examiner*—Donald G. Daus
*Assistant Examiner*—M. C. Eakin
*Attorney, Agent, or Firm*—Carl A. Cline

[57] ABSTRACT

A novel class of compounds which are useful as plant growth regulators is disclosed, having the general structural formula:

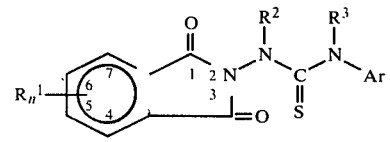

in which
$R^1$ is; $C_1$ to $C_4$ alkyl, nitro or halo and n is zero or an integer from 1 to 4
$R^2$ and $R^3$ are; H or $C_1$ to $C_4$ alkyl or hydroxyalkyl, or benzyl and
Ar is; adamantyl, $C_3$ to $C_4$ alkyl or alkenyl, benzyl, halobenzyl, naphthyl, phenyl or phenyl bearing thereon from one to three of the substituents: cyano, benzyloxy, methylenedioxy, nitro, bromo, chloro, trifluoromethyl and $C_1$ to $C_4$ alkyl, alkenyl, alkoxy, alkylthio and alkyl-substituted amino.

69 Claims, No Drawings

N-(ARYLTHIOCARBAMOYL)-2-AMINO-1H-ISOINDOLE-1,3-(2H)DIONES AND USE AS PLANT GROWTH REGULATORS

CROSS REFERENCE TO RELATED APPLICATIONS

The present application is a continuation-in-part of U.S. patent application Ser. No. 19,065, filed Mar. 9, 1979, now abandoned.

DESCRIPTION OF THE INVENTION

Growth regulating effects have been observed upon application of many chemical substances to plants. In general, very few of these substances can be used with benefit to the plants which are effected. In most instances the beneficial effects, if any, are minor and the major effects are so drastic that the compounds can only be used for the destruction of the plants. Examples of growth regulator compounds with drastic effects which have become useful as herbicides are 2,4-D, EPTC and alachlor. Among the potential commercial uses for growth regulator compounds with less drastic effects are the following:

Increase or induce flowering (pineapple).
Increase blossom set, pod set, seed set, and/or fruit set (prevent abortion of flowers or withered blossoms).
Increase size of fruits, vegetables, seed, and/or tubers (grapes, soybeans, sugar beets, etc.).
Decrease size of fruit, vegetables, seed, and/or tubers (potatoes, and grapefruits).
Increase number of tillers (cereals).
Increase number of shoots from crown (alfalfa).
Increase branching (soybeans) or widen branches (apples).
Reduce height (shortened internodes) in crops and ornamentals (cereals and mums).
Growth retardent (turf, cotton, perennial legumes in no-till corn).
Enhance yields of corn by larger ears, better filled ears and/or more ears per plant.
Increase nutritive value of seeds, fruits, vegetables, forages, etc. (protein content).
Reduce transpiration (drought resistance).
Reduce respiration (potatoes or sugar beets in storage).

We have discovered a group of novel compounds which display a great variety of growth regulating effects, indicating utility for many purposes, including uses mentioned above. The present invention is directed to these novel compounds, including methods of manufacture, as well as methods and formulations for plant growth regulation.

Briefly, the novel class of growth regulator compounds has the general structural formula:

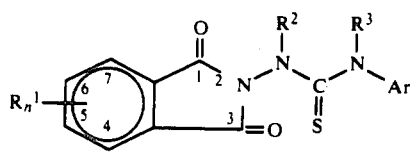

in which
$R^1$ is; $C_1$ to $C_4$ alkyl, nitro or halo and n is zero or an integer from 1 to 4

$R^2$ and $R^3$ are; H or $C_1$ to $C_4$ alkyl or hydroxyalkyl, or benzyl and

Ar is; adamantyl, $C_3$ to $C_4$ alkyl or alkenyl, benzyl, halobenzyl, naphthyl, phenyl or phenyl bearing thereon from one to three of the substituents: cyano, benzyloxy methylenedioxy, nitro, bromo, chloro, trifluoromethyl and $C_1$ to $C_4$ alkyl, alkenyl, alkoxy, alkylthio and alkyl-substituted amino.

The aforementioned compounds are employed to regulate the growth of plants by applying an effective amount to the plants, the seed or the soil, preferably in combination with an inert carrier or diluent and a surface active agent, according to customary practice in the art.

SYNTHESIS OF THE GROWTH REGULATORS

The novel compounds of this invention may be produced from commercially available raw materials by means of procedures based on those outlined and specifically illustrated below:

The synthesis of N-(phenylthiocarbamoyl or substituted phenylthiocarbamoyl)-2-amino-1H-isoindole-1,3-(2H)dione (III), that is, the case of Structure I where $R_1$, $R_2$ and $R_3$ all are hydrogen, has been accomplished by reacting 2-amino-1H-isoindole-1,3-(2H)dione (II) with the corresponding aryl isothiocyanates. The preparation of starting material (II) was accomplished by the reaction of phthalimide with hydrazine in alcohol at <5° C. to give (II) in ~70% yield with high purity. The literature procedure, J. Chem. Soc., 587 (1937), requires heating to reflux and gives a low (~45%) yield.

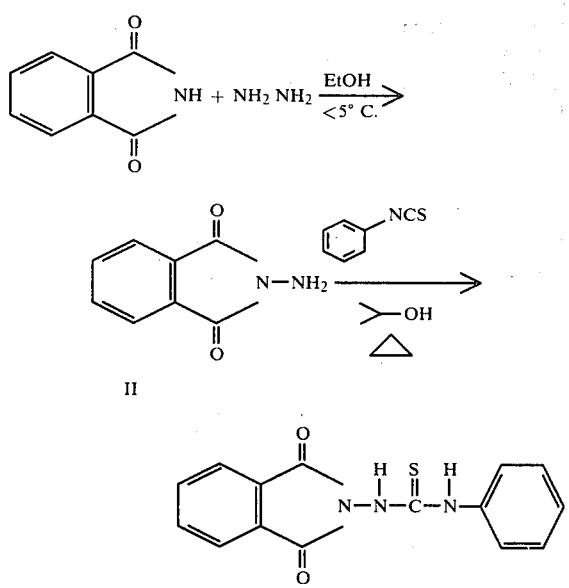

In the case of Structure (I) with n being equal to zero and $R_2$ being alkyl, special methods of preparation are required, as discussed below.

N-Methyl-N-(phenylthiocarbamoyl)-2-amino-1H-isoindole-1,3-(2H)-dione (IV) has been prepared by the cyclization of 2-(2-carboxybenzoyl)-1-methyl-N-phenylhydrazinethiocarboxamide with N,N'-dicyclohexylcarbodiimide, as outlined below:

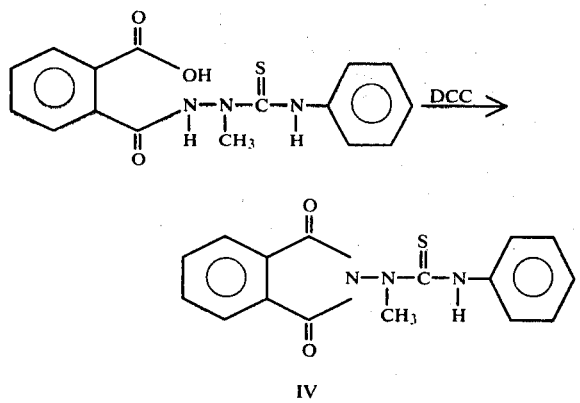

IV

According to two other schemes, the desired compounds were formed from intermediate compounds of the formula

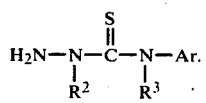

N-Methyl-N-(phenyl-N-methylthiocarbamoyl)-2-amino-1H-isoindole-1,3-(2H)dione (VI) was obtained in a single step by reacting phthalic anhydride with N,1-dimethyl-N-phenylhydrazinethiocarboxamide (V) in chloroform. Similarly, commercially available ring substituted phthalic anhydrides and substituted 2-carbomethoxybenzoyl chlorides, made by conventional methods may be condensed with N-methyl and 1-methylhydrazinethiocarboxamides to give the corresponding specific compounds of formula (I), as in the following outline of synthesis procedures.

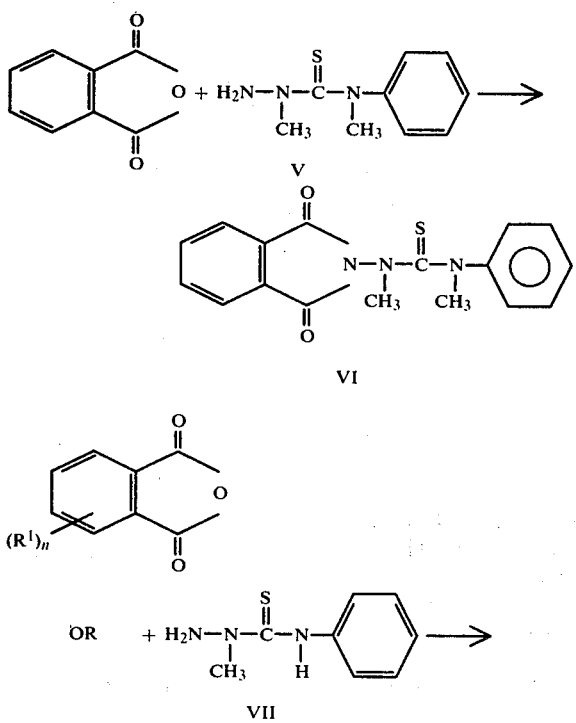

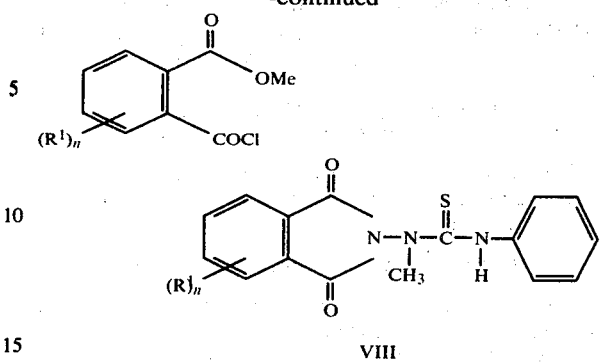

VIII

Below are specific illustrative procedures. The identity of the product was confirmed in each example by means of infrared and nuclear magnetic resonance spectra. All melting points are uncorrected.

2-Amino-1H-isoindole-1,3-(2H)dione (II)

To an ice-cold suspension of 14.7 g (0.1 mole) of phthalimide in 100 ml of 95% ethyl alcohol at 5° C., with stirring, 3.6 ml (0.11 mole) of 96.8% hydrazine was added dropwise. A slight exothermic reaction was observed and the mixture was allowed to stir at 5° C. for two hours. The mixture was diluted with 200 ml of ice water, stirred, filtered, washed with water and dried to give 12.2 g (75%) of white powder, m.p. 199°–202°.

Recrystallization from methanol-water gave white needles, m.p. 201°–203°.

N-(Phenylthiocarbamoyl)-2-amino-1H-isoindole-1,3-(2H)dione (III)

To a suspension of 8.2 g (0.05 mole) of II in 50 ml of dry 2-propanol, 6 ml (0.05 mole) of phenyl isothiocyanate was added. The mixture was stirred and refluxed for 3 hours, allowed to cool to room temperature and poured into 300 ml of 50% ethyl alcohol. After stirring for one hour, the solid which formed was filtered, washed with water and dried to give 12.1 g (81%) of the desired product as a white powder, m.p. 180°–181°.

N-Methyl-N-(phenylthiocarbamoyl)-2-amino-1H-isoindole-1,3-(2H)dione (IV)

Method 1

To an ice-cold solution of 8.25 g (0.025 mole) of 2-(2-carboxybenzoyl)-1-methyl-N-phenylhydrazinethiocarboxamide in 225 ml of 1,2-dimethoxyethane at ~2° C., a solution of 5.5 g (0.027 mole) of N,N'-dicyclohexylcarbodiimide was added dropwise below 5° C. with stirring. The mixture was stirred in an ice bath and then left at room temperature overnight. The mixture was filtered to remove N,N'-dicyclohexylurea and the filtrate was evaporated below 40° C., under vacuum, to give a yellow amorphous solid which was stirred in 100 ml of dry ether and warmed gently. The ether solution was allowed to stand for a few hours and filtered to give 4.6 g (59%) of whitish yellow crystals, m.p. 142°–144°.

Recrystallization from ethyl acetone-hexane gave whitish crystals, m.p. 151°–153°.

Mass spectrum: M+311

Intermediate compounds of the type represented by the formula

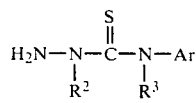

may be made by procedures of the type which are specifically illustrated below.

N,1-Dimethyl-N-phenylhydrazinethiocarboxamide (V)

To a solution of N-methyl-N-phenylthiocarbamyl chloride 79.6 g (0.43 m) in 250 ml dry ether, a solution of 39.5 g (0.86 m) methylhydrazine in 100 ml of dry ether was added dropwise with stirring below 10° C. The reaction temperature was allowed to increase to room temperature and filtered. The filtrate was evaporated to low volume and diluted with ~300 ml hexane. After stirring for a few hours the hexane layer was decanted. The hexane immiscible layer was reevacuated to remove organic solvents, giving the desired product, 70.0 g as a thick orange liquid.

1-Methyl-N-phenylhydrazinethiocarboxamide (VII) is prepared by a procedure similar to the foregoing. The following procedure is illustrative of the preparation of an intermediate in which $R^2$ is H.

N-Methyl-N-phenylhydrazinethiocarboxamide

To a solution of 7.7 g (0.24 m) anhydrous hydrazine in 200 ml of dry ether, N-methyl-N-phenylthiocarbamyl chloride 20.4 g (0.11 m) was added below 5° C. with stirring. The mixture was stirred and allowed to warm to room temperature. The mixture was filtered and the residue resuspended in ~100 ml water and stirred. Filtration gave 8.8 g of the desired product as whitish powder, m.p. 121°-22°.

The following procedures are illustrative of the use of the intermediates of the formula

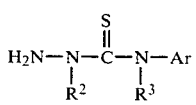

N-Methyl-N-(phenylthiocarbamoyl)-2-amino-4-methyl-1H-isoindole-1,3-(2H)dione (VIII)

To a solution of 6.8 g (0.037 mole) of 1-methyl-N-phenylhydrazinethiocarboxamide (VII) and 3.0 g of pyridine in 100 ml dry dimethoxyethane, 2-carbomethoxy-6-methylbenzoyl chloride (8.0 g, 0.037 mole) was added and the resulting mixture was stirred at room temperature for 60 hours. The solvent was distilled and the residue was taken up in ethyl acetate, filtered and dried on anhydrous magnesium sulfate. Removal of the solvent gave 10 g (83%) of the desired product, m.p. 110°-115° (dec.).

N-Methyl-N-(phenyl-N-methylthiocarbamoyl)-2-amino-1H-isoindole-1,3-(2H)dione (VI)

To a slurry of 5.9 g (0.04 mole) of phthalic anhydride in 50 ml of dry chloroform, N,1-dimethyl-N-phenylhydrazinethiocarboxamide (7.8 g, 0.04 mole) (V) was added dropwise with stirring at room temperature to give an exothermic reaction. The mixture was stirred at room temperature overnight to give a clear solution. The solution was diluted with ~250 ml of hexane to give an oily product. Decantation of the organic layer and extraction of the residue with 3×50 ml of anhydrous ether, filtration of the ether extracts and dilution with hexane precipitated the desired product. Filtration, washing with hexane and drying gave 8.6 g (66%) of solid, m.p. 175°-176°.

Use of the Growth Regulators

In highly active compounds, phytotoxic effects of pre-emergent and post-emergent application are often readily apparent. These effects may be demonstrated by means of the following illustrative procedures.

Pre-emergent Application

Disposable paper trays about 2½ inches deep were filled with soil and sprayed with aqueous spray mixtures at a rate of 5 lb. of active chemical per acre of sprayed area, were seeded with 6 species of plant seeds and were then covered with about ¼ inch of soil. The spray mixtures were prepared by dissolving the proper amount of growth regulator compound in 15 ml of acetone, adding 4 ml of a solvent-emulsifier mixture consisting of 60 wt. percent of a commercial polyoxyethylated vegetable oil emulsifier (96 wt. percent active ingredient, Emulphor EL-719), 20 wt. percent xylene and 20 wt. percent deodorized kerosene, then bringing total volume up to 60 ml by addition of warm water. Twenty-one days after seeding and treatment the plantings were examined and plant injury was rated according to the following schedule:

DEGREE OF EFFECT

0 = no effect
1 = slight effect, plants recovered
2 = moderate effect, injury to 26 to 75 percent
3 = severe effect, injury to 76 to 99 percent of foliage
4 = maximum effect (all plants died)

Post-emergent Application

Several species of plants were grown in potting soil in disposable styrofoam trays and tomatoes were grown in four-inch pots in the greenhouse. Aqueous spray formulations were prepared and the growing plants were sprayed at a spray volume of 60 gallons per acre and an application rate of 5 lb. per acre. Spray mixtures were prepared in the manner described above. For comparative purposes, plants were also sprayed at 60 gal./acre with a spray mixture containing no growth regulator. Plant injury was again rated according to the schedule disclosed above and observations of growth regulator effects were observed and recorded as follows:

| Effect | Abbreviation in Tables |
|---|---|
| Formative effect on new growth | F |
| Epinasty | E |
| Growth reduction | G |
| Non-emergence | K |
| Necrosis | N |

In Table I below there are tabulated various compounds which have been made according to the above illustrative procedures, as well as observations of pre- and post-emergent herbicidal and growth regulator effects.

TABLE I
EFFECTS ON PLANT SPECIES
of Compounds of the formula

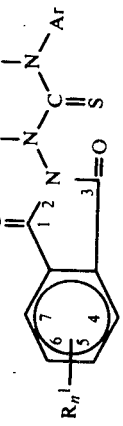

| Comp'd. No. | $R_n^1$ | $R^2$ | $R^1$ | Ar | M.P. | Preemergent Effects ||||||| Postemergent Effects ||||||| Comments on Utility |
| --- | --- | --- | --- | --- | --- | --- | --- | --- | --- | --- | --- | --- | --- | --- | --- | --- | --- | --- | --- |
| | | | | | | Crab-grass | Cox-comb | Brome | Millet | Radish | Sugar beet | Millet | Alfalfa | Oat | Radish | Sugar beet | Tomato | |
| 2431 | n = 0 | H | H | phenyl | 180–1° | 0 | F3G2 | F3G1 | F2G1 | F1 | F2G1 | F2 | F3G2 | F2 | F1 | F3G1 | F1 increased fruiting | Growth reduction |
| 2459 | n = 0 | H | H | 4-CH₃ phenyl | 190° Dec. | F1G1 | 0 | F1 | 0 | 0 | F2G2 | 0 | F2 | 0 | G1 | F2G2 | N1 | Growth reduction |
| 2460 | n = 0 | H | H | 4-F phenyl | 180° Dec. | F1G1 | G1 | F1 | 0 | F1 | F1G1 | 0 | F1 | 0 | F2 | N2F1 | 0 | Growth reduction |
| 2461 | n = 0 | H | H | 3-CH₃ phenyl | 175° Dec. | | G2 | F2 | F3G3 | F2G2 | F1G1 | N3G2 | F3G3 | 0 | F2G1 | F2G1 | N1 | Growth reduction |
| 2462 | n = 0 | H | H | 2-Cl phenyl | 175° Dec. | 0 | K3 | F1 | 0 | F1 | F1 | 0 | N3G3 | 0 | N1F1 | F2G2 | 0 | Suppression of foxtail and millet |
| 2654 | n = 0 | CH₃ | H | phenyl | 151–3° | K4 | F3G3 | K4 | F3G3 | F3G3 | F3G3 | N3G2 | N4 | N2G2 | — | N4 | F2 | Growth reduction. Cotton defoliant. Promotes tillering of rice, oats, wheat. Inhibitors of tasseling. |
| 2457 | 4NO₂ | H | H | phenyl | 90–2° | F2G2 | 0 | F1G1 | 0 | 0 | 0 | 0 | 0 | 0 | 0 | 0 | 0 | Pre-emergent herbicide |
| 2759 | 5-CH₃ | CH₃ | H | phenyl | 102–5° | 0 | 0 | 0 | 0 | 0 | 0 | 0 | F1 | 0 | 0 | F1 | F1 | Post-emergent growth regulant |
| 2769 | 4-CH₃ | H | H | phenyl | 189–92° | F3G3 | F2F2 | F2 | F2G1 | F2G2 | F1 | F1 | F2 | F1 | F1G1 | F2 | F3E1 | Growth promoter (oats and tomato) |
| 2770 | 4-CH₃ | CH₃ | H | phenyl | 110–150° | F3G3 | F2G2 | F3G2 | F3G3 | F3G3 | F3G2 | F1 | F3 | F1 | F1 | F2 | F3E3 | Promotes fruit set on tomato. Pre-emergent herbicide |
| 2791 | n = 0 | CH₃ | H | 3-F phenyl | ~65° | K4 | F3G2 | F3G3 | F3G3 | F3G2 | F3G2 | G3G3 | F3G3 E1 | F3G2 | F3G2 | F3G3 | F3G2 E3 | Promotes tillering of oats. Pre-emergent herbicide |
| 2792 | n = 0 | CH₃ | H | 4-F phenyl | ~55° | K4 | F3G2 | F3G2 | F3G3 | F3G2 | F2G2 | F2G2 | F3G˙ | F2 | F2G1 | F3G2 | F3G3 | Promotes tillering of oats. Pre-emergent herbicide |
| 2797 | n = 0 | CH₃ | CH₃ | phenyl | 175–6° | 0 | 0 | 0 | 0 | 0 | F1G1 | 0 | F1 | 0 | 0 | F2 | F2 | Growth regulant |
| 2857 | n = 0 | CH₂CH₃ | H | phenyl | ~60° | K4 | K4 | F3G3 | N2G2 | F3G2 | F3G3 | N2G2 | F2G2 | F2G2 | F1 | F2G2 | F1G1 | Promotes tillering of oats. Pre-emergent herbicide |
| 2858 | n = 0 | H | CH₃ | phenyl | ~170° Dec. | F2G3 | F1G1 | F2G1 | F2G2 | F1G1 | F2G2 | 0 | F1 | 0 | N1 | F2G2 | F1 | Controls crabgrass Growth regulant |
| 2864 | 4,7-di Cl | CH₃ | H | phenyl | 169–73° | 0 | G1 | 0 | 0 | 0 | G2 | 0 | 0 | 0 | 0 | F2G1 | 0 | Growth regulant |

TABLE I-continued

EFFECTS ON PLANT SPECIES
of Compounds of the formula

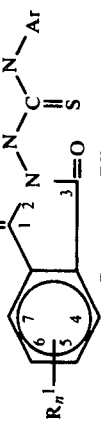

| Comp'd. No. | $R_n^1$ | $R^2$ | $R^3$ | Ar | M.P. | Crab-grass | Cox-comb | Brome | Millet | Radish | Sugar beet | Millet | Alfalfa | Oat | Radish | Sugar beet | Tomato | Comments on Utility |
|---|---|---|---|---|---|---|---|---|---|---|---|---|---|---|---|---|---|---|
| | | | | | | | | Preemergent Effects | | | | | | Postemergent Effects | | | | |
| 2866 | 4-F | H | H | phenyl | 185–7° | F1 | 0 | F1 | E1 | F2G1 | 0 | 0 | 0 | 0 | F1 | F2 | F1 | Growth regulant |
| 2904 | n = 0 | H | H | 3-F phenyl | 162–5° | F1 | F2G1 | K4 | F3G2 | F2G1 | G1 | N1 | N1F1 | N1G1 | F2G1 | F2G2 | 0 | Combats cheat grass in grain fields. |
| 2906 | n = 0 | H | H | 3-CF₃ phenyl | 149–152° | G1 | 0 | 0 | 0 | 0 | 0 | 0 | F1 | 0 | N1G2 | F2 | N1F1 | Growth regulant |
| 2907 | n = 0 | H | H | 3-Cl phenyl | 158–61° | F2G1 | F2G1 | F2 | F2G1 | F1 | F1G1 | G1 | F2G1 | 0 | F1 | F2G1 | 0 | Growth regulant |
| 2920 | 4-CH₃ | CH₃ | CH₃ | phenyl | 174–75° | 0 | N2 | F2 | G1 | 0 | 0 | N1 | 0 | 0 | 0 | 0 | 0 | Growth regulant |
| 2973 | n = 0 | H | H | 2,4-dimethyl phenyl | 196–8° | F1G1 | F2G1 | F2 | F1 | 0 | K2 | N1 | F1G1 | 0 | F1 | F2G2 | 0 | Growth regulant |
| 2974 | n = 0 | H | H | 3-Cl, 4-CH₃ phenyl | 188–90° | F1G1 | K2 | F2 | 0 | F2G1 | K2 | 0 | F1 | 0 | F1 | F1G1 | 0 | Growth regulant |
| 2975 | n = 0 | H | H | 3,4-di Cl phenyl | 185–87° | 0 | K1 | F2 | F1G1 | F1 | K2 | 0 | F2 | 0 | F1 | F1G1 | F1G1 | Growth regulant |
| 2978 | n = 0 | H | H | 1-naphthyl | 168–71° | 0 | 0 | 0 | 0 | 0 | 0 | 0 | 0 | 0 | F1 | 0 | F1 | Growth regulant |
| 3059 | n = 0 | H | H | 2,5-dichloro-phenyl | 183–4° | 0 | 0 | F1 | 0 | 0 | 0 | N1 | F1 | 0 | N1 | F2G1 | 0 | Growth regulant |
| 3061 | n = 0 | H | H | 4-Br-phenyl | 200–2° | 0 | 0 | F2 | F2G1 | F1 | 0 | 0 | F3 | 0 | F1 | F1 | F2 | Growth regulant |
| 3112 | n = 0 | CH₃ | H | 2,6-dimethyl-phenyl | 156–160° | 0 | F1 | 0 | 0 | 0 | F2G2 | 0 | 0 | 0 | 0 | F2G1 | 0 | |
| 3113 | n = 0 | H | H | adamantyl | 160–163 | 0 | 0 | 0 | 0 | 0 | 0 | 0 | N2 | N1 | G1 | 0 | N1 | |
| 3198 | n = 0 | CH₃ | H | 2,3-dimethyl-phenyl | | F2G2 | F1 | F3G1 | F3G2 | F1 | F2G2 | 0 | 0 | 0 | 0 | F2G2 | F3 | |
| 3199 | n = 0 | CH₃ | H | 2,4,5-trimethyl-phenyl | — | 0 | 0 | 0 | 0 | 0 | 0 | 0 | 0 | 0 | 0 | F2G1 | 0 | |
| 3200 | n = 0 | CH₃ | H | 2,5-dimethyl-phenyl | — | F1 | F1 | F2 | F2G1 | F1 | F1 | 0 | 0 | 0 | 0 | F2G2 | 0 | |
| 3202 | n = | benzyl | H | phenyl | 155–158 | 0 | 0 | F2 | 0 | 0 | 0 | 0 | F1 | 0 | 0 | F2G1 | F2 | |
| 3203 | n = 0 | CH₃ | H | tert.butyl | 203–205 | 0 | 0 | 0 | 0 | 0 | 0 | 0 | 0 | 0 | 0 | F1 | 0 | |
| 3404 | n = 0 | CH₃ | H | 4-nitrophenyl | 157–160 | F1G1 | K2 | F3G1 | F1G1 | F2G2 | F2G2 | 0 | F2G2 | 0 | F1 | F3 | F2 | |
| 3405 | n = 0 | CH₃ | H | 3-chloro-4-methylphenyl | | F1G1 | K4 | F3G2 | F2G2 | F3G2 | F2G2 | 0 | 0 | F1 | F2G1 | F3 | F3 | |
| 3406 | n = 0 | CH₃ | H | 3,4-dimethyl-phenyl | 179–182 | F2G2 | K4 | F3G3 | F3G2 | F3G2 | F3G3 | 0 | 0 | 0 | F1G1 | F1G1 | F1 | |
| 3407 | n = 0 | CH₃ | H | 3,5-dimethyl-phenyl | 153–156 | F2G2 | K4 | F3G3 | F3G2 | F3G2 | F3G3 | 0 | F2G2 | F1 | F2G2 | F3G1 | F2 | |
| 3197 | n = 0 | (CH₂)₂OH | H | phenyl | — | 0 | 0 | K4 | F3G3 | F3G2 | F3G2 | 0 | F2 | 0 | 0 | F2 | 0 | |
| 3408 | n = 0 | CH₃ | H | 3-ethylphenyl | 74–78 | F2G2 | K4 | F2G3 | F3G2 | F2G1 | F3G1 | 0 | F3G3 | 0 | F2G2 | F3G1 | F3 | |
| 3412 | n = 0 | H | H | 4-chlorophenyl | 197–199 | F2G1 | F2G2 | K4 | F3G2 | F3G1 | F2G1 | 0 | 0 | 0 | F2G2 | F3G2 | F1 | |
| 3496 | 4,5,6,7 tetrachloro | CH₃ | H | phenyl | >100 | 0 | 0 | 0 | 0 | 0 | 0 | 0 | 0 | 0 | 0 | G1 | 0 | |
| 3626 | n = 0 | H | H | allyl | 173–75 | F1G1 | 0 | F3G2 | G1 | 0 | F2 | 0 | 0 | 0 | 0 | F1 | 0 | |

TABLE I-continued
EFFECTS ON PLANT SPECIES
of Compounds of the formula

| Comp'd. No. | $R_n^1$ | $R^2$ | $R^3$ | Ar | M.P. | Preemergent Effects ||||||| Postemergent Effects ||||||| Comments on Utility |
|---|---|---|---|---|---|---|---|---|---|---|---|---|---|---|---|---|---|---|---|
| | | | | | | Crab-grass | Cox-comb | Brome | Millet | Radish | Sugar beet | | Millet | Alfalfa | Oat | Radish | Sugar beet | Tomato | |
| 3726 | n = 0 | H | H | 4-methoxyphenyl | 197-199 | 0 | 0 | 0 | 0 | 0 | 0 | | 0 | F1 | 0 | 0 | F2 | N1 | |
| 3727 | n = 0 | H | H | 2-methyl-3-chlorophenyl | 153-155 | 0 | 0 | 0 | 0 | 0 | 0 | | 0 | 0 | 0 | 0 | F2 | 0 | |
| 3729 | n = 0 | H | H | 4-isopropylphenyl | 150-152 | 0 | 0 | 0 | 0 | 0 | 0 | | 0 | 0 | 0 | 0 | F1 | 0 | |
| 3730 | n = 0 | H | H | 2-chloro-6-methylphenyl | 170-172 | 0 | 0 | 0 | 0 | 0 | 0 | | 0 | 0 | 0 | 0 | F1 | 0 | |
| 3810 | n = 0 | CH3 | H | 4-methoxyphenyl | 170-172 | 0 | F2G1 | F3G3 | F2 | F2G2 | F2G1 | | 0 | F2G1 | F1G1 | F2G1 | F3G1 | F2 | |
| 3811 | n = 0 | CH3 | H | 2-chloro-4-methylphenyl | 66-69 | 0 | 0 | F2G2 | 0 | F2G1 | F1G1 | | 0 | F1 | 0 | 0 | F2G1 | F1 | |
| 3821 | n = 0 | CH3 | H | 4-chlorophenyl | 164-170 | F2G1 | K4 | K4 | F3G2 | K4 | K4 | | F2G3 | F3G3 | F2G2 | F3G3 | F3G3 | F3G1 | |
| 3825 | n = 0 | H | H | 3-benzyloxyphenyl | 158-160 | 0 | 0 | F1 | 0 | 0 | 0 | | 0 | 0 | 0 | 0 | F1 | 0 | |
| 3826 | n = 0 | H | H | 3-nitrophenyl | 184-187 | 0 | 0 | 0 | 0 | 0 | 0 | | — | F1 | 0 | F1 | F1 | F1 | |
| 3827 | n = 0 | H | H | 4-benzyloxyphenyl | 194-196 | 0 | 0 | F1 | 0 | 0 | 0 | | 0 | F1 | 0 | 0 | 0 | 0 | |
| 3828 | n = 0 | H | H | 4-chloro-3-trifluoromethylphenyl | 181-183 | 0 | 0 | F1 | 0 | 0 | 0 | | F2 | F2 | 0 | F3G2 | F1 | F1 | |
| 3829 | n = 0 | H | H | 2,4-dichlorophenyl | 196-198 | F2G2 | F3G3 | F2G3 | F3G2 | F2G1 | F3G2 | | F2 | F3G2 | F2 | F3G2 | F3G2 | F2 | |
| 3831 | n = 0 | H | H | 2-trifluoromethylphenyl | 166-169 | 0 | 0 | F1 | 0 | F1G1 | 0 | | 0 | F1 | 0 | N1G1 | N1G1 | N1 | |
| 3832 | n = 0 | H | H | 3-chlorobenzyl | 187-189 | 0 | 0 | 0 | 0 | F1G1 | 0 | | 0 | 0 | 0 | F1 | F1 | F1 | |
| 3833 | n = 0 | H | H | 3-methoxyphenyl | 163-165 | F2G1 | K4 | F1 | F2G2 | 0 | F2G2 | | F1G1 | F3G2 | F1 | F2G1 | F3G1 | F3 | |
| 3870 | 4-fluoro | CH3 | H | 3,5-dimethylphenyl | 45 | — | — | K4 | — | F2G2 | F2G2 | | 0 | F3G3 | F1G1 | F1G1 | F3G3 | F3 | |
| 3948 | n = 0 | H | H | 3-methylthiophenyl | 188-190 | — | — | — | — | — | — | | 0 | 0 | 0 | F1G1 | F1 | 0 | |
| 3949 | n = | H | H | 2-chloro-4-methylphenyl | 70-73 | | | | | | | | 0 | 0 | 0 | 0 | 0 | 0 | |
| 3950 | n = 0 | H | H | 4-cyanophenyl | 187-189 | | | | | | | | 0 | F2 | 0 | 0 | F2G1 | F1 | |
| 3954 | n = 0 | H | H | 4-diethylaminophenyl | 230-231 | | | | | | | | 0 | 0 | 0 | 0 | F1 | 0 | |
| 3955 | n = 0 | H | H | 4-trifluoromethylphenyl | 198-199 | | | | | | | | 0 | 0 | 0 | 0 | F1 | F1 | |
| 3956 | n = 0 | H | H | 4-chloro-2-methylphenyl | 93-96 | | | | | | | | 0 | 0 | 0 | 0 | 0 | 0 | |
| 3957 | n = 0 | H | H | 4-ethoxyphenyl | 197-199 | | | | | | | | F1 | F3G3 | F1 | F3G2 | F3G2 | F2 | |
| 3958 | n = 0 | H | H | 4-ethoxyphenyl | 189-190 | | | | | | | | F1 | F3G3 | 0 | F1 | F2G1 | F2 | |
| | | | | | | | | | | | | | 0 | 0 | 0 | 0 | F2 | F1 | |

TABLE I-continued
EFFECTS ON PLANT SPECIES
of Compounds of the formula
| Comp'd. No. | $R_n^1$ | $R^2$ | $R^3$ | Ar | M.P. | Preemergent Effects | | | | | Postemergent Effects | | | | | Comments on Utility |
|---|---|---|---|---|---|---|---|---|---|---|---|---|---|---|---|---|
| | | | | | | Crab-grass | Cox-comb | Brome | Millet | Radish | Sugar beet | Millet | Alfalfa | Oat | Radish | Sugar beet | Tomato | |
| 3959 | n = 0 | H | H | 2-fluorophenyl | | | | | | | F1 | F1 | 0 | F1 | F3G1 | F1 | |
| 3960 | n = 0 | H | H | 3,4-methylene-dioxyphenyl | 208–209 | | | | | | | 0 | 0 | 0 | 0 | F1 | 0 |

The use of many of the growth regulator compounds may be demonstrated by treatment of soybeans (soja max) to increase the number of seed pods and by treating tomato plants (*Lycopersicum esculentum*) to increase fruit set. In an illustrative experiment, *Soja max* (Evans variety) and *Lycopersicum esculentum* (Tiny Tim variety) were grown in 4-inch pots (one plant per pot) filled with greenhouse potting soil (2 parts good top soil, 1½ parts builders' sand, 1½ parts peat, fertilized with 5 lb. of 12-12-6 fertilizer and 5 lb. of finely ground limestone per cu. yd.). Aqueous spray formulations were prepared and the potted plants were sprayed at a spray volume of 40 gal. per acre and at application rates of 16, 4, 1 and ¼ oz. per acre. The spray mixtures were prepared by dissolving the proper amount of growth regulator compound in 15 ml. of acetone, adding 2 ml. of a solvent-emulsifier mixture consisting of 60 wt. percent of a commercial polyoxyethylated vegetable oil emulsifier (96 wt. percent active ingredient, Emulphor EL-719), 20 wt. percent xylene and 20 wt. percent deodorized kerosene, then bringing total volume up to 80 ml by addition of a 0.156 wt. percent aqueous solution of liquid non-ionic dispersant (90 wt. percent active trimethylnonyl polyethylene glycol ether, Tergitol TMN-10). Two replicates were sprayed at all application rates. For comparative purposes, plants were also sprayed at 40 gal./acre with water. The number of seed pods and of fruit as percentage of arithmetic mean of the numbers on untreated plants was observed within approximately three weeks after spray treatment and the results are tabulated below. The severity of growth regulatory effect on the plants was estimated on a scale of 0 to 10 and is also recorded in the following table:

| GROWTH REGULATING EFFECTS ON TWO SPECIES | | | | |
|---|---|---|---|---|
| | | *Soja max* | | *Lycopersicum esculentum* Fruit |
| Comp'd. No. | Rate oz/A. | Pod Count[1] Percent in Comparison to Untreated Plants | Severity of Growth Regulating Effect[2] | Count Percent in Comparison to Untreated Plants | Severity of Growth Regulating Effect[2] |
|---|---|---|---|---|---|
| 2431 | 16 | 120 | 2.5 | 150 | 0.5 |
|  | 4 | 105 | 0 | 150 | 0 |
|  | 1 | 90 | 0 | 117 | 0 |
| 2459 | 16 | 153 | 7 | 117 | 1.5 |
|  | 4 | 117 | 1 | 117 | 0 |
|  | 1 | 102 | 0 | 150 | 0 |
| 2460 | 16 | 177 | 4.5 | 117 | 0 |
|  | 4 | 135 | 1.5 | 67 | 0 |
|  | 1 | 111 | 0 | 100 | 0 |
| 2461 | 16 | 126 | 6 | 67 | 0.5 |
|  | 4 | 129 | 1 | 133 | 0 |
|  | 1 | 105 | 0 | 67 | 0 |
| 2462 | 16 | 109 | 1.5 | 254 | 2 |
|  | 4 | 92 | 1 | 162 | 0 |
|  | 1 | 106 | 0 | 69 | 0 |
| 2654 | 16 | 183 | 9 | 291 | 8 |
|  | 4 | 151 | 4 | 255 | 7.5 |
|  | 1 | 134 | 1.5 | 327 | 2.5 |
| 2769 | 16 | 95 | 6.5 | 162 | 1 |
|  | 4 | 102 | 1 | 231 | 0 |
|  | 1 | 92 | 0 | 69 | 0 |
| 2770 | 16 | 124 | 7 | 462 | 8.5 |
|  | 4 | 138 | 2 | 392 | 5.5 |
|  | 1 | 116 | 1 | 531 | 1 |
| 2791 | 16 | 171 | 9 | 182 | 9 |
|  | 4 | 134 | 5.5 | 255 | 7.5 |
|  | 1 | 120 | 2 | 364 | 3.5 |
| 2792 | 16 | 131 | 7.5 | 300 | 8 |
|  | 4 | 141 | 2 | 369 | 5.5 |
|  | 1 | 127 | 1 | 462 | 2.5 |
| 2857 | 16 | 116 | 8.5 | 208 | 8.5 |
|  | 4 | 131 | 2 | 554 | 5.5 |
|  | 1 | 106 | 1 | 508 | 2.5 |
| 2858 | 16 | 102 | 4 | 162 | 0.5 |
|  | 4 | 106 | 0.5 | 69 | 0 |
|  | 1 | 106 | 0 | 162 | 0 |
| 2866 | 16 | 109 | 0 | 277 | 0.5 |
|  | 4 | 95 | 0 | 162 | 0 |
|  | 1 | 99 | 0 | 69 | 0 |
| 2904 | 16 | 129 | 2.5 | 109 | 0 |
|  | 4 | 117 | 0 | 109 | 0 |
|  | 1 | 100 | 0 | 73 | 0 |
| 2906 | 16 | 165 | 4 | 117 | 0.5 |
|  | 4 | 105 | 1 | 133 | 0 |
|  | 1 | 96 | 0 | 100 | 0 |
| 2907 | 16 | 138 | 7 | 83 | 2.5 |
|  | 4 | 111 | 1.5 | 150 | 0 |
|  | 1 | 87 | 0 | 200 | 0 |
| 2920 | 16 | 102 | 0 | 162 | 0 |
|  | 4 | 99 | 0 | 92 | 0 |
|  | 1 | 102 | 0 | 115 | 0 |
| 2973 | 16 | 102 | 0.5 | 185 | 0 |
|  | 4 | 99 | 0 | 162 | 0 |
|  | 1 | 109 | 0 | 69 | 0 |
| 2974 | 16 | 123 | 5.5 | 50 | 0.5 |
|  | 4 | 120 | 2 | 100 | 0 |
|  | 1 | 96 | 0 | 117 | 0 |
| 2975 | 16 | 132 | 4 | 100 | 1 |
|  | 4 | 132 | 0.5 | 133 | 0 |
|  | 1 | 102 | 0 | 50 | 0 |
| 2978 | 16 | 113 | 1.5 | 300 | 0.5 |
|  | 4 | 92 | 0 | 162 | 0 |
|  | 1 | 106 | 0 | 115 | 0 |
| 2982 | 16 | 113 | 1 | 69 | 0 |
|  | 4 | 106 | 0 | 115 | 0 |
|  | 1 | 109 | 0 | 162 | 0 |
| 3059 | 16 | 117 | 0 | 67 | 0 |
|  | 4 | 105 | 0 | 100 | 0 |
|  | 1 | 93 | 0 | 100 | 0 |
| 3061 | 16 | 168 | 8 | 100 | 0.5 |
|  | 4 | 174 | 6.5 | 33 | 0 |
|  | 1 | 141 | 1 | 117 | 0 |
| 3112 | 16 | 94 | 2 | 66 | 0.5 |
|  | 4 | 105 | 0 | 75 | 0 |
|  | 1 | 101 | 0 | 122 | 0 |
| 3197 | 16 | 105 | 0 | 84 | 0 |
|  | 4 | 101 | 0 | 131 | 0 |
|  | 1 | 101 | 0 | 75 | 0 |
| 3198 | 16 | 94 | 1.5 | 150 | 1.5 |
|  | 4 | 105 | 0 | 150 | 1 |
|  | 1 | 98 | 0 | 94 | 0 |
| 3199 | 16 | 120 | 0.5 | 141 | 0.5 |
|  | 4 | 105 | 0 | 131 | 0 |
|  | 1 | 109 | 0 | 66 | 0 |
| 3200 | 16 | 128 | 1 | 131 | 1.5 |
|  | 4 | 105 | 0 | 75 | 0 |
|  | 1 | 109 | 0 | 84 | 0 |
| 3202 | 16 | 101 | 1 | 122 | 0.5 |
|  | 4 | 98 | 0 | 150 | 0 |
|  | 1 | 109 | 0 | 150 | 0 |
| 3404 | 16 | 94 | 2.5 | 113 | 8 |
|  | 4 | 105 | 0 | 150 | 3 |
|  | 1 | 105 | 0 | 122 | 0 |
| 3405 | 16 | 109 | 0 | 103 | 6 |
|  | 4 | 98 | 0 | 113 | 1 |
|  | 1 | 94 | 0 | 66 | 0.5 |
| 3406 | 16 | 101 | 0.5 | 103 | 3.5 |
|  | 4 | 105 | 0 | 84 | 1 |
|  | 1 | 94 | 0 | 122 | 0 |
| 3412 | 16 | 129 | 4 | 176 | 1 |
|  | 4 | 104 | 1.5 | 141 | 0 |

| GROWTH REGULATING EFFECTS ON TWO SPECIES | | | | |
|---|---|---|---|---|
| | | Soja max | Lycopersicum esculentum Fruit | |
| Comp'd. No. | Rate oz/A. | Pod Count[1] Percent in Comparison to Untreated Plants | Severity of Growth Regulating Effect[2] | Count Percent in Comparison to Untreated Plants | Severity of Growth Regulating Effect[2] |
| | 1 | 100 | 0 | 71 | 0 |
| 3821 | 16 | 162 | 8.5 | 577 | 8.5 |
| | 4 | 155 | 4.5 | 438 | 6.5 |
| | 1 | 141 | 2.5 | 323 | 6 |
| 3829 | 16 | 173 | 5.5 | 141 | 5.5 |
| | 4 | 154 | 1.5 | 159 | 2 |
| | 1 | 128 | 0 | 103 | 0.5 |

[1]Check = 100
[2]Greenhouse rating on scale of 0, no effect; 10, total kill.

The information presented in tabular form herein will enable a worker in the art to make a selection from among the growth regulator compounds of the invention and to make some judgment with regard to application rates, depending upon the effect which is desired. It may be seen, for example, that total kills of some species of vegetation may occur at application rates as high as 5 to 10 lb. per acre, whereas beneficial effects may be observed on living plants at application rates of 1 lb. per acre or less.

The growth regulator compounds are usually applied in combination with inert carriers or diluents, as in aqueous sprays, granules and dust formulations in accordance with established practice in the art. An aqueous spray is usually prepared by mixing a wettable powder or emulsifiable concentrate formulation of a growth regulator with a relatively large amount of water to form a dispersion.

Wettable powders comprise intimate, finely divided mixtures of growth regulator compounds, inert solid carriers and surface active agents. The inert solid carrier is usually chosen from among the attapulgite clays, the kaolin clays, the montmorillonite clays, the diatomaceous earths, finely divided silica and purified silicates. Effective surfactants, which have wetting, penetrating and dispersing ability are usually present in a wettable powder formulation in proportions of from 0.5 to about 10 percent by weight. Among the surface active agents commonly used for this purpose are the sulfonated lignins, naphthalenesulfonates and condensed naphthalenesulfonates, alkylbenzenesulfonates, alkyl sulfates and non-ionic surfactants such as products of condensation of ethylene oxide with alkylphenols.

Emulsifiable concentrates of the growth regulator compounds comprise in each instance, a solution of growth regulator compound in a liquid carrier which is a mixture of water-immiscible solvent and surfactants, including emulsifiers. Useful solvents include aromatic hydrocarbon solvents such as the xylenes, alkylnaphthalenes, petroleum distillates, terpene solvents, ether-alcohols and organic ester solvents. Suitable emulsifiers, dispersing and wetting agents may be selected from the same classes of products which are employed in formulating wettable powders.

In general, the growth regulators are applied in formulations which desirably contain from 0.1 percent to 95 percent of a compound of formula (1) and from 0.1 to 75 percent of a carrier or surfactant. However, direct application to plant seeds prior to planting may be accomplished in some instances by mixing powdered solid growth regulator with seed to obtain a substantially uniform coating which is very thin and comprises only one or two percent by weight or less, based on the weight of the seed. In most instances, however, a non-phytotoxic solvent, such as methanol is employed as a carrier to facilitate the uniform distribution of growth regulator on the surface of the seed.

When a compound is to be applied to the soil, as for a pre-emergence application, granular formulations are sometimes more convenient than sprays. A typical granular formulation comprises the growth regulator compound dispersed on an inert carrier such as coarsely ground clay, or clay which has been converted to granules by treatment of a rolling bed of the powdered material with a small amount of liquid in a granulating drum. In the usual process for preparing granular formulations, a solution of the active compound is sprayed on the granules while they are being agitated in a suitable mixing apparatus, after which the granules are dried with a current of air during continued agitation.

We claim:

1. Compounds which have the structural formula:

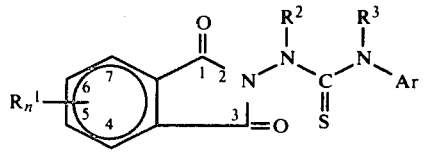

in which

R[1] is; $C_1$ to $C_4$ alkyl, nitro or halo and n is zero or an integer from 1 to 4

R[2] and R[3] are; H or $C_1$ to $C_4$ alkyl or hydroxyalkyl, or benzyl and

Ar is; adamantyl, $C_3$ to $C_4$ alkyl or alkenyl, benzyl, halobenzyl, naphthyl, phenyl or phenyl bearing thereon from one to three of the substituents: cyano, benzyloxy, methylenedioxy, nitro, bromo, chloro, trifluoromethyl and $C_1$ to $C_4$ alkyl, alkenyl, alkoxy, alkylthio and alkyl-substituted amino.

2. N-(Phenylthiocarbamoyl)-2-amino-1H-isoindole-1,3-(2H)dione.

3. N-(4-Methylphenylthiocarbamoyl)-2-amino-1H-isoindole-1,3-(2H)dione.

4. N-(4-Fluorophenylthiocarbamoyl)-2-amino-1H-isoindole-1,3-(2H)dione.

5. N-(3-Methylphenylthiocarbamoyl)-2-amino-1H-isoindole-1,3-(2H)dione.

6. N-(2-Chlorophenylthiocarbamoyl)-2-amino-1H-isoindole-1,3-(2H)dione.

7. N-Methyl-N-(phenylthiocarbamoyl)-2-amino-1H-isoindole-1,3-(2H)dione.

8. 4-Nitro-N-(phenylthiocarbamoyl)-2-amino-1H-isoindole-1,3-(2H)dione.

9. 5-Methyl-N-methyl-N-(phenylthiocarbamoyl)-2-amino-1H-isoindole-1,3-(2H)dione.

10. 4-Methyl-N-(phenylthiocarbamoyl)-2-amino-1H-isoindole-1,3-(2H)dione.

11. 4-Methyl-N-methyl-N-(phenylthiocarbamoyl)-2-amino-1H-isoindole-1,3-(2H)dione.

12. N-Methyl-N-(3-fluorophenylthiocarbamoyl)-2-amino-1H-isoindole-1,3-(2H)dione.

13. N-Methyl-N-(4-fluorophenylthiocarbamoyl)-2-amino-1H-isoindole-1,3-(2H)dione.

14. N-Methyl-N-(N-methylphenylthiocarbamoyl)-2-amino-1H-isoindole-1,3-(2H)dione.
15. N-Ethyl-N-(phenylthiocarbamoyl)-2-amino-1H-isoindole-1,3-(2H)dione.
16. N-(N-Methylphenylthiocarbamoyl)-2-amino-1H-isoindole-1,3-(2H)dione.
17. 4,7-Dichloro-N-methyl-N-(phenylthiocarbamoyl)-2-amino-1H-isoindole-1,3-(2H)dione.
18. 4-Fluoro-N-(phenylthiocarbamoyl)-2-amino-1H-isoindole-1,3-(2H)dione.
19. N-(3-Fluorophenylthiocarbamoyl)-2-amino-1H-isoindole-1,3-(2H)dione.
20. N-(3-Trifluoromethylphenylthiocarbamoyl)-2-amino-1H-isoindole-1,3-(2H)dione.
21. N-(3-Chlorophenylthiocarbamoyl)-2-amino-1H-isoindole-1,3-(2H)dione.
22. N,4-Dimethyl-N-(N-methylphenylthiocarbamoyl)-2-amino-1H-isoindole-1,3-(2H)dione.
23. N-(2,4-Dimethylphenylthiocarbamoyl)-2-amino-1H-isoindole-1,3-(2H)dione.
24. N-(3-Chloro-4-methylphenylthiocarbamoyl)-2-amino-1H-isoindole-1,3-(2H)dione.
25. N-(3,4-Dichlorophenylthiocarbamoyl)-2-amino-1H-isoindole-1,3-(2H)dione.
26. N-(1-Naphthylthiocarbamoyl)-2-amino-1H-isoindole-1,3-(2H)dione.
27. N-(2,5-Dichlorophenylthiocarbamoyl)-2-amino-1H-isoindole-1,3-(2H)dione.
28. N-(4-Bromophenylthiocarbamoyl)-2-amino-1H-isoindole-1,3-(2H)dione.
29. N-Methyl-N-(2,6-dimethylphenylthiocarbamoyl)-2-amino-1H-isoindole-1,3-(2H)dione.
30. N-(Adamantylthiocarbamoyl)-2-amino-1H-isoindole-1,3-(2H)dione.
31. N-Hydroxyethyl-N-(phenylthiocarbamoyl)-2-amino-1H-isoindole-1,3-(2H)dione.
32. N-Methyl-N-(2,3-dimethylphenylthiocarbamoyl)-2-amino-1H-isoindole-1,3-(2H)dione.
33. N-Methyl-N-(2,4,5-trimethylphenylthiocarbamoyl)-2-amino-1H-isoindole-1,3-(2H)dione.
34. N-Methyl-N-(2,5-dimethylphenylthiocarbamoyl)-2-amino-1H-isoindole-1,3-(2H)dione.
35. N-Benzyl-N-(phenylthiocarbamoyl)-2-amino-1H-isoindole-1,3-(2H)dione.
36. N-Methyl-N-tert.butylthiocarbamoyl-2-amino-1H-isoindole-1,3-(2H)dione.
37. N-Methyl-N-(4-nitrophenylthiocarbamoyl)-2-amino-1H-isoindole-1,3-(2H)dione.
38. N-Methyl-N-(3-chloro-4-methylphenylthiocarbamoyl)-2-amino-1H-isoindole-1,3-(2H)dione.
39. N-Methyl-N-(3,4-dimethylphenylthiocarbamoyl)-2-amino-1H-isoindole-1,3-(2H)dione.
40. N-Methyl-N-(3,5-dimethylphenylthiocarbamoyl)-2-amino-1H-isoindole-1,3-(2H)dione.
41. N-Methyl-N-(3-ethylphenylthiocarbamoyl)-2-amino-1H-isoindole-1,3-(2H)dione.
42. N-(4-chlorophenylthiocarbamoyl)-2-amino-1H-isoindole-1,3-(2H)dione.
43. N-Methyl-N-(phenylthiocarbamoyl)-2-amino-4,5,6,7-tetrachloro-1H-isoindole-1,3-(2H)dione.
44. N-Allylthiocarbamoyl-2-amino-1H-isoindole-1,3-(2H)dione.
45. N-(4-Methoxyphenylthiocarbamoyl)-2-amino-1H-isoindole-1,3-(2H)dione.
46. N-(2-Methyl-3-chlorophenylthiocarbamoyl)-2-amino-1H-isoindole-1,3-(2H)dione.
47. N-(4-Isopropylphenylthiocarbamoyl)-2-amino-1H-isoindole-1,3-(2H)dione.
48. N-(2-Chloro-6-methylphenylthiocarbamoyl)-2-amino-1H-isoindole-1,3-(2H)dione.
49. N-Methyl-N-(4-methoxyphenylthiocarbamoyl)-2-amino-1H-isoindole-1,3-(2H)dione.
50. N-Methyl-N-(2-chloro-4-methylphenylthiocarbamoyl)-2-amino-1H-isoindole-1,3-(2H)dione.
51. N-Methyl-N-(4-chlorophenylthiocarbamoyl)-2-amino-1H-isoindole-1,3-(2H)dione.
52. N-(3-Benzyloxyphenylthiocarbamoyl)-2-amino-1H-isoindole-1,3-(2H)dione.
53. N-(3-Nitrophenylthiocarbamoyl)-2-amino-1H-isoindole-1,3-(2H)dione.
54. N-(4-Benzyloxyphenylthiocarbamoyl)-1H-isoindole-1,3-(2H)dione.
55. N-(4-Chloro-3-trifluoromethylphenylthiocarbamoyl)-2-amino-1H-isoindole-1,3-(2H)dione.
56. N-(2,4-Dichlorophenylthiocarbamoyl)-2-amino-1H-isoindole-1,3-(2H)dione.
57. N-(2-Trifluoromethylphenylthiocarbamoyl)-2-amino-1H-isoindole-1,3-(2H)dione.
58. N-(3-Chlorobenzylthiocarbamoyl)-2-amino-1H-isoindole-1,3-(2H)dione.
59. N-(3-Methoxyphenylthiocarbamoyl)-2-amino-1H-isoindole-1,3-(2H)dione.
60. N-Methyl-N-(phenylthiocarbamoyl)-2-amino-4-fluoro-1H-isoindole-1,3-(2H)dione.
61. N-(3,5-Dimethylphenylthiocarbamoyl)-2-amino-1H-isoindole-1,3-(2H)dione.
62. N-(3-Methylthiophenylthiocarbamoyl)-2-amino-1H-isoindole-1,3-(2H)dione.
63. N-(2-Chloro-4-methylphenylthiocarbamoyl)-2-amino-1H-isoindole-1,3-(2H)dione.
64. N-(4-Cyanophenylthiocarbamoyl)-2-amino-1H-isoindole-1,3-(2H)dione.
65. N-(4-Trifluoromethylphenylthiocarbamoyl)-2-amino-1H-isoindole-1,3-(2H)dione.
66. N-(4-Chloro-2-methylphenylthiocarbamoyl)-2-amino-1H-isoindole-1,3-(2H)dione.
67. N-(4-Ethoxyphenylthiocarbamoyl)-2-amino-1H-isoindole-1,3-(2H)dione.
68. N-(2-Fluorophenylthiocarbamoyl)-2-amino-1H-isoindole-1,3-(2H)dione.
69. N-(3,4-Methylenedioxyphenylthiocarbamoyl)-2-amino-1H-isoindole-1,3-(2H)dione.

* * * * *